United States Patent [19]

Schmidt et al.

[11] Patent Number: 4,842,776
[45] Date of Patent: Jun. 27, 1989

[54] STYRYLARYLOXY ETHER SULFONATES, A PROCESS FOR THEIR PREPARATION AND THEIR USE IN THE RECOVERY OF CRUDE OIL

[75] Inventors: Manfred Schmidt, Kelkheim; Walter Rupp; Gerhart Schneider, both of Königstein; Eva M. Kohn, Bad Soden am Taunus, all of Fed. Rep. of Germany

[73] Assignee: Hoechst Aktiengesellschaft, Frankfurt am Main, Fed. Rep. of Germany

[21] Appl. No.: 112,560

[22] Filed: Oct. 22, 1987

[30] Foreign Application Priority Data

Oct. 24, 1986 [DE] Fed. Rep. of Germany ....... 3636277

[51] Int. Cl.$^4$ ............................................. C07C 143/29
[52] U.S. Cl. ............................ 260/512 C; 260/512 R
[58] Field of Search ....................... 260/512 R, 512 C

[56] References Cited

U.S. PATENT DOCUMENTS

| 3,827,497 | 8/1974 | Dycus et al. | 252/8.55 D |
|---|---|---|---|
| 3,977,471 | 8/1976 | Gale et al. | 252/8.55 D |
| 4,018,278 | 4/1977 | Shupe | 252/8.55 D |
| 4,077,471 | 3/1978 | Shupe et al. | 252/8.55 D |
| 4,088,189 | 5/1978 | Shupe | 166/272 |
| 4,194,564 | 3/1980 | Schievelbein | 166/274 |
| 4,318,816 | 3/1982 | Schievelbein | 252/8.55 D |
| 4,600,516 | 7/1986 | Wester et al. | 252/8.55 D |

FOREIGN PATENT DOCUMENTS

| 3347578 | 7/1985 | Fed. Rep. of Germany . |
|---|---|---|
| 1560346 | 2/1980 | United Kingdom . |
| 1579167 | 12/1980 | United Kingdom . |

Primary Examiner—Nicky Chan

[57] ABSTRACT

Styrylaryloxy ether sulfonates of the formula

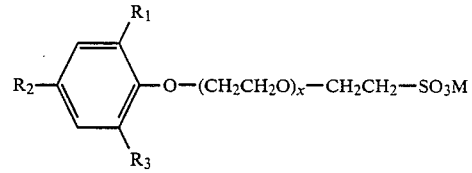

in which either $R_1$ denotes styryl and simultaneously $R_2$ and $R_3$ are identical or different and denote hydrogen or styryl, or $R_1$ and $R_2$ are nonidentical and each denote methyl or styryl and simultaneously $R_3$ denotes hydrogen or styryl, x denotes a number from 2 to 20, and M denotes an ammonium or alkali metal cation. These compounds are suitable as surfactant auxiliaries in oil recovery.

2 Claims, No Drawings

STYRYLARYLOXY ETHER SULFONATES, A PROCESS FOR THEIR PREPARATION AND THEIR USE IN THE RECOVERY OF CRUDE OIL

DESCRIPTION

Styrylaryloxy ether sulfonates, a process for their preparation, and their use in the recovery of crude oil.

The invention relates to novel styrylaryloxy ether sulfonates, their preparation, and their use as surfactants, in particular for tertiary recovery of crude oil, and also synergistic surfactant combinations.

In the recovery of oil from underground reservoirs, it is generally only possible to recover 20–30% of the oil originally present by primary recovery methods. In these, the oil reaches the surface with the aid of the natural reservoir pressure. In secondary recovery, water is forced into the geological formation and the oil is recovered through several production wells. This water flooding as a secondary measure is relatively inexpensive and is therefore used frequently, but in many cases only leads to slightly increased recovery of oil from the reservoir.

When the secondary oil recovery measures have been completed, a further economic recovery of oil can only be achieved by introducing mechanical energy. In the heterogeneous pore space, the water, which has a relatively low viscosity, passes the oil, which has a relatively high viscosity, so that virtually only water and no more oil is recovered. If the degree of water invasion at about 98% has exceeded the economic limit, only tertiary oil recovery methods are suitable. These are taken to mean methods in which either the viscosity of the oil is reduced and/or the interfacial tension between water and oil is reduced.

Most methods can be classified as thermal oil recovery methods, solution or mixture flooding, or surfactant or polymer flooding, or as combinations of several of the methods mentioned. In thermal recovery methods, steam or hot water is injected into the reservoir or in situ combustion takes place. In solution or mixture methods, a solvent for the crude oil (gas or a liquid) is injected into the reservoir.

Surfactant flooding methods are based on a considerable decrease in the interfacial tension between the oil and the flooding water. Depending on the surfactant concentration, a distinction is made between surfactant flooding (low-tension flooding), micelle flooding and emulsion flooding.

In the monograph by D. O. Shah and R. S. Schechter: Improved Oil Recovery by Surfactant and Polymer Flooding, Academic Press Inc., New York, and in numerous patent specifications, a large number of surfactants are listed which can be used in the surfactant flooding process. Surfactants which are described here are, above all, sulfonates, such as, for examples, synthetic and natural petroleumsulfonates, alkylsulfonates, such as, for example, Na $C_{13}$–$C_{18}$-sec-alkanesulfonate MW 328/350, Na α-olefin-sulfonate and Na (vinylidene)olefinsulfonate, alkylarylsulfonate, such as, for example, Na dodecylbenzenesulfonate, alkyltoluenesulfonates or alkylxylenesulfonates. However, these sulfonates only have a very low tolerance limit for the salt content of the reservoir water. Thus, for example, petroleumsulfonates are soluble only in water having a salt content of 1.5% of NaCl.

Sulfonates are also very sensitive, above all, to the alkaline earth metals contained in the reservoir of water. When these surfactants are used at relatively high salt concentrations, precipitation products are formed which can lead to blockage of the porous spaces of the formation. Many reservoirs have relatively high salinity, for example 25% in northern Germany. In order to be able to work with sulfonates in these reservoir systems, combinations with alcohols and/or nonionic surfactants (alkyl or alkylaryl polyglycol ethers) are proposed which are stable at these salt concentrations, but the oil-mobilizing action has usually been worsened.

U.S. Pat. No. 3,827,497 proposes the use of salts of sulfated oxyalkylated alcohols. However, it has been shown that salts which contain the COS bond are hydrolytically cleaved at elevated temperatures. U.S. Pat. Nos. 4,018,278, 4,088,189, 4,077,471, 4,120,228, 4,318,816, 4,194,564, 4,318,816 and 3,977,471 describe ether sulfonates ($C_{12}$–$C_{15}$-alkyl- and alkylaryl ether sulfonates) which are stable in reservoir water having a high salt content (200 g/l) and at a reservoir temperature up to 120° C. However, an oil-mobilizing action with the aid of the surfactants can only be determined in selected reservoirs. Similar results have been experienced using the alkyl ether propane sulfonate and alkyl ether glycidyl ether sulfonate products described in German Offenlegungsschrift No. 2,724,442 and German Offenlegungsschrift No. 2,724,490. The use in oil recovery of tributyl phenol ether glycidyl sulfonates and tributyl ether sulfonates is also known (German Offenlegungsschrift No. 3,347,578 and German Offenlegungsschrift No. 3,346,676).

Individual reservoirs differ in the temperature, which can be between 20° and 120° C., in the oil composition, which can be paraffinic, naphthenic, aromatic, high-, medium- or low-viscosity, in the salt content and the salt composition, which can be between 3% and 25% of NaCl with various contents of alkaline earth metals, in the reservoir formation, the minerological composition (for example sandstone or limestone), porosity and permeability. The object is therefore to find surfactants or surfactant combinations which are effective under the maximum number of reservoir conditions present (ie. in the temperature range from 20° to 120° C., and a salt content from 30 to 250 g/l) and for the various types of oil.

It has now been found that styryl phenol or cresol ether sulfonates are effective when used as surfactants for oil recovery at various reservoir parameters.

The invention relates to styrylaryloxy ether sulfonates of the formula

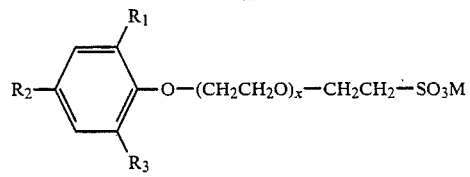

in which either $R_1$ denotes styryl and simultaneously $R_2$ and $R_3$ are identical or different and denote hydrogen or styryl, or $R_1$ and $R_2$ are nonidentical and each denote methyl or styryl and simultaneously $R_3$ denotes hydrogen or styryl, x denotes a number from 2 to 20, preferably 2 to 12, and M denotes an ammonium or alkali metal cation.

Preference is given to styryl cresol ether sulfonates of the above formula in which $R_1$ and $R_2$ are nonidentical and each denote methyl or styryl, and $R_3$ denotes hydrogen or styryl, and x and M have the abovementioned meanings. The styryl radical is in all cases taken to mean a group of the formula

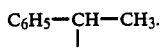

These compounds are prepared according to the following reaction equation:

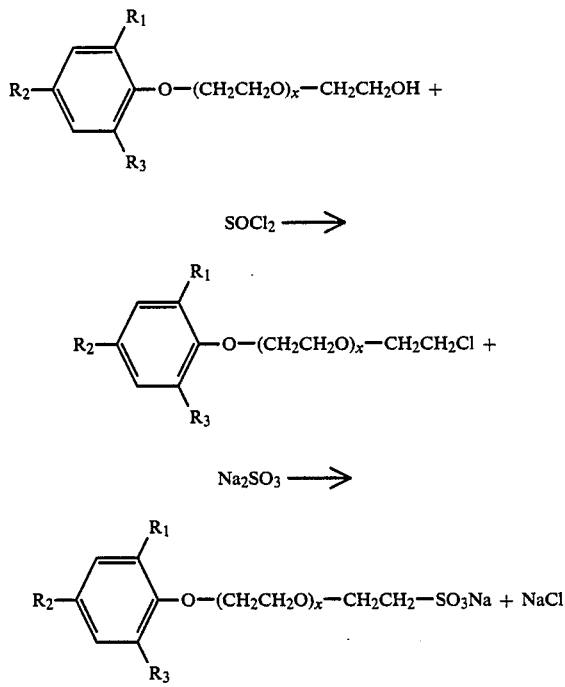

The reaction of the intermediate compound with sodium sulfite takes place at 130° to 190° C., preferably 160°–180° C., in aqueous solution, if appropriate together with cosolvents such as lower alcohols (isopropanol or butanol), glycols or glycol ethers. In order to increase the yield, it is advantageous to add a small amount of the final product from a previous batch to the reaction batch. It is also possible to use potassium sulfite in place of sodium sulfite.

The mono- and di-styrylphenol and -cresol ether sulfonates of the above formula are surfactants which are distinguished by stability in a broad temperature and pH range. Aqueous solutions of these compounds reduce the surface tension at the surfactant solution/air phase interface to values in the order of about 40 mNm$^{-1}$ (according to Du Nouy) and the oil/surfactant solution interfacial tension to values of about 10$^{-2}$ mNm$^{-1}$ (spinning drop interfacial tensiometer). As a consequence of their activity and stability over a broad pH range, these compounds are suitable for alkaline and acidic metal cleaning agents and fire extinguishing agents. In addition, they are effective emulsifiers for emulsion polymerization and are suitable as stabilizers for latex and other polymer emulsions. Also of particular interest is the use of these compounds in tertiary oil recovery and in well stimulation and formation fracturing of crude oil reservoirs. Use of the compounds of the present invention increases the oil yield in this process.

In all cases, the surfactant is generally employed in amounts of 0.01 to 10, preferably 0.05 to 3%.

The styrylphenol and -cresol ether sulfonates according to the invention may particularly advantageously be employed in combination with other anionic surfactants, such as, for example, olefinsulfonates, alkanesulfonates, α-olefinsulfonates, internal olefinsulfonates, alkylarylsulfonates, dodecylbenzenesulfonates, petroleumsulfonates, alkylxylenesulfonates, alkyltoluenesulfonates and nonionic surfactants of alkyl- or alkylphenyl polyglycol ethers. Of particular interest here are mixtures of the mono- or di-styrylcresol ether sulfonates according to the invention and alkanesulfonates or olefinsulfonates and/or petroleumsulfonates in the mixing ratio 4:1 to 1:4. Further suitable additives are alcohols, glycol ethers, alkylglycol ethers and dialkylglycol ethers. In addition, the viscosity of flooding water can be increased by polymers such as, for example, hydroxyethylcellulose, polyacrylamides, copolymers based on acrylamide, or polysaccharides.

EXAMPLE 1

Na monostyryl-o-cresol(6 EO)-sulfonate (Na α-phenylethyl-o-cresol(6 EO)-sulfonate)

120 g (0.245 mol) of the chloride (7.25% of organically bound chlorine) prepared from α-phenylethyl-o-cresol(6 EO)-polyglycol ether by OH/Cl substitution by means of thionyl chloride, are transferred into a 0.7 liter stirred autoclave with 37 g of sodium sulfite, 230 g of water, 5 g of isopropanol, 50 g of sulfonate solution from a previous batch and, if appropriate, NaOH to pH 9–10, and the mixture is stirred for 6 hours at 175° C. The product obtained contains 27.9% of sulfonate, which corresponds to a yield of 80.0% (relative to the chloride employed) and a sulfonate molecular weight of 558.

EXAMPLE 2

Na monostyryl-p-cresol(8 EO)-sulfonate 140 g (0.25 mol) of the chloride (6.35% of organically bound chlorine) prepared from α-phenylethyl-p-cresol(8 EO)-polyglycol ether by OH/Cl substitution by means of thionyl chloride are transferred into a 0.7 liter stirred autoclave with 36 g of sodium sulfite, 260 g of water, 5 g of isopropanol, 50 g of a sulfonate solution from a previous batch and, if appropriate, NaOH to pH 9–10, and the mixture is stirred for 6 hours at 175° C. The product obtained contains 28.0% of sulfonate, which corresponds to a yield of 79% (relative to the chloride employed) and a sulfonate molecular weight of 627.

EXAMPLE 3

Na distyryl-o-cresol(13 EO)-sulfonate (Na di-α-phenylethyl-o-cresol(13 EO) sulfonate)

140 g (0.155 mol) of di-α-phenyl-o-cresol(13 EO) chloride (3.9% of organically bound chlorine) are transferred into a 0.7 liter stirred autoclave with 24 g of sodium sulfite, 280 g of water, 5 g of isopropanol, 50 g of sulfonate solution from a previous batch and, if appropriate, NaOH to pH 9–10, and the mixture is stirred for 6 hours at 175° C. The product obtained contains 27.6% of sulfonate, this corresponds to a yield of 81.6% (relative to the chloride employed) and a sulfonate molecular weight of 974.

EXAMPLE 4

Na distyryl-p-cresol(17 EO)-sulfonate

(Na α-phenylethyl-p-cresol(17 EO)-sulfonate)

120 g (0.1 mol) of di-α-phenylethyl-p-cresol(17 EO) chloride (3.3% of organically bound chlorine) are transferred into a 0.7 liter stirred autoclave with 17 g of sodium sulfite, 200 g of water, 5 g of isopropanol, 50 g of sulfonate solution from a previous batch and, if appropriate, NaOH to pH 9-10, and the mixture is stirred for 6 hours at 175° C. The product obtained contains 28.8% of sulfonate, which corresponds to a yield of 77.8% (relative to the chloride employed) and a sulfonate molecular weight of 1150.

In order to determine the effectiveness of the compounds according to the invention and of the synergistic surfactant combination, the microcapillary oil removal method described in U.S. Pat. No. 4,008,165, determination of the interfacial tension by the spinning drop interfacial tensiometer method, the phase behavior in accordance with Winsor and Laboratory flooding experiments in glass tubes filled with sand are employed.

In microcapillary oil removal, glass microcapillaries from Drummond Scientific Co./USA which have a volume of 5 μl, a length of 30 mm and a diameter of 0.45 mm are used as a model of the pore space in the reservoir.

The microcapillaries are sealed at one end by melting, evacuated in a desiccator and filled with crude oil. The capillaries are introduced vertically, with the opening facing up, into surfactant solutions (test tubes) whose temperatures are controlled in a waterbath, and the displacement of oil is recorded visually as a function of time.

With the aid of the following assessment table, the effectiveness of the surfactants can be determined as a function of their concentration, the salt concentration, pH, temperature and oil composition.

Value
9 empty (30 mm) after 10 minutes
8 empty after 1 hour
7 empty after 3 hours
6 empty after 20 hours
5 16-25 mm emptying after 20 hours
4 9-15 mm emptying after 20 hours
3 4-8 mm emptying after 20 hours
2 1-3 mm emptying after 20 hours
1 trace emptying after 20 hours
0 unchanged after 20 hours This method has the advantage that, with the low diameter of the microcapillaries, the viscosity and the density of the oils do not greatly influence the oil removal action and it is possible to work with reservoir oil and reservoir water.

According to Taber, J. Petr. Techn. 3 (1969), pp. 3-12, surfactants are suitable for tertiary oil recovery only if the interfacial tension at the oil/salt water phase interface is reduced to values of less than $10^{-2}$ mNm$^{-1}$. For determining the interfacial tension at the oil/water phase interface, the spinning drop interfacial tensiometer developed by Wade and Burkowsky is used. (M. Burkowsky and C. Marx: Über den Mechanismus des Tensidflutens in hochsalinaren Systemen [On the Mechanism of Surfactant Flooding in High-Saline Systems]; Erd/öL-Erdgas-Zeitschrift 95 (1979), pp. 17-25).

The method is based on the fact that an oil drop which is introduced into a capillary rotating about the horizontal axis and which contains a liquid (salt water and surfactant) of relatively high density is deformed. The drop is extended until equilibrium of the deforming forces and the interfacial tension is reached.

The interfacial tension is calculated according to Vonnegut (B. Vonnegut, Rev. Sci. Instruments 13 (1942), pp. 6-9) from the measured oil drop diameter R, the rotation speed W and the density difference Δd, according to the following formula:

$$\gamma_{\frac{1}{2}} = \frac{\Delta d \cdot W^2 \cdot R^3}{4} \quad (mNm^{-1})$$

According to the current explanation of the mechanism of oil removal in surfactant flooding, the formation of a 3rd phase (middle phase) of a microemulsion is the prerequisite for an optimum surfactant flooding result [Rieckmann, M., "Tertiäre Erdölgewinnung" [Tertiary Oil Recovery], Erdöl und Kohle-Erdgas-Petrochemie, 36 (1983) 281-282, Healy, R. N. and Reed, R. L., Soc. Petr. Eng. J. 10 (1979) 492-501, Obah, B. and Neumann, J. H. "über die Bildung von Mikroemulsionen" [On the Formation of Microemulsions], Tenside Detergents 20 (1983) 145-151]. This desired third phase arises in the system when the interfacial tension at the oil/salt water phase interface is greatly reduced.

When determining the middle phases, 5 ml of surfactant solution (with salt water) and 5 ml of oil (reservoir oil or model oil) are introduced into a test tube, the test tube is sealed by melting, shaken vigorously and stored in a drying cabinet at constant temperature. After a storage time of one hour, the test tubes are again shaken vigorously and then stored without further mixing. After a storage time of 1 and 7 days, the formation of the phases (middle phase) is determined.

A further important selection criterion is the oil-mobilizing action of the styryl ether sulfonates which is investigated in laboratory flooding experiments. Suitable experimental conditions are flooding experiments using artificial sand, sandstone or limestone beds which are introduced into glass tubes. When carrying out the experiments, quartz sand of certain grain sizes are shaken into Quickfit glass tubes (length: 15 cm, internal diameter: 2.6 cm) with the aid of a vibrator. The sand-filled flooding tube is provided with a frit, seal and cover plate and tested for leaks. The tubes are filled with degassed formation water, the physical data, porosity and permeability are determined according to Darcy's Law and subsequently soaked in oil. The tubes are heated, and injection water can be injected after calibrating the pressure gauge and checking the feed rates of the injection pumps. Surfactant or polymer flooding commences when the oil yield remains constant over a relatively long period of time (about 1.5 to 2.0 PV). After the chemical slog, the amount of which depends on the concentration, the viscosity, economic efficiency etc., flooding water is again injected. The flooding experiment is complete when no oil or only very little oil is flooded out. The amounts of water and oil brought out (recovered) are determined volumetrically and plotted against the pore volume (oil recovery curve).

The values measured using these methods are collated in the tables below. In all cases, 1% strength aqueous solutions of the surfactants were employed. (Exceptions are given). In all examples, "EO" denotes ethylene oxide. In all cases, the alkanesulfonate used in the examples has a molecular weight of 328, and the alkylxylene-sulfonate has a molecular weight of 390.

Example 1
Surface tension according to Du Nouy (mNm$^{-1}$)
(25° C./40° C.)

| | Dist. water (72.6/70.0 mNm$^{-1}$) 0.5% | | 50 g/l of NaCl (76/74 mNm$^{-1}$) 0.5% | |
|---|---|---|---|---|
| | 25° C. | 40° C. | 25° C. | 40° C. |
| Na monostyryl-o-cresol(6 EO) ether sulfonate | 43.4 | 44.8 | 41.9 | 43.2 |
| Na monostryl-o-cresol(8 EO) ether sulfonate | 45.8 | 45.8 | 43.3 | 43.8 |
| Na distyryl-o-cresol(15 EO) ether sulfonate | 46.4 | 46.2 | 43.7 | 44.2 |
| Na monostyryl-p-cresol(8 EO) ether sulfonate | 43.5 | 43.1 | 41.0 | 42.2 |
| Na distyryl-p-cresol(17 EO) ether sulfonate | 48.0 | 45.0 | 44.7 | 43.9 |

Example 2
Interfacial tension according to Du Nouy (mNm$^{-1}$)
at room temperature (RT), pH = 6.5, content of active substance (A$_S$) = 0.5%

| | Dist. water/n-octane (50.8/51.1 mNm$^{-1}$) | 50 g/l of NaCl/n-octane (43.6 mNm$^{-1}$) |
|---|---|---|
| Na monostyryl-o-cresol(6 EO) ether sulfonate | 9.0 | 5.5 |
| Na monostyryl-o-cresol(8 EO) ether sulfonate | 9.0 | 6.0 |
| Na distyryl-o-cresol(15 EO) ether sulfonate | 8.4 | 6.3 |
| Na monostyryl-p-cresol(8 EO) ether sulfonate | 9.0 | 6.0 |
| Na distyryl-p-cresol(17 EO) ether sulfonate | 10.6 | 7.0 |

Example 3
Interfacial tension according to Du Nouy (mNm$^{-1}$)
at RT, pH 6.5, AS = 0.5%

| | Dist. water/toluene (34.0/34.8 mNm$^{-1}$) | 50 g/l of NaCl/toluene (33.3/33.5 mNm$^{-1}$) |
|---|---|---|
| Na monostyryl-o-cresol(6 EO) ether sulfonate | 4.9 | 1.5 |
| Na monostyryl-o-cresol(8 EO) ether sulfonate | 4.6 | 1.9 |
| Na distyryl-o-cresol(15 EO) ether sulfonate | 4.5 | 2.5 |
| Na monostyryl-p-cresol(8 EO) ether sulfonate | 4.5 | 1.6 |
| Na distyryl-p-cresol(17 EO) ether sulfonate | 5.0 | 2.4 |

Example 4
Interfacial tension according to Du Nouy (mNm$^{-1}$)
at 40° C., pH 6.5, AS = 0.5%

| | Dist. water/toluene (32.5 mNm$^{-1}$) | 50 g/l of NaCl/toluene (30.5 mNm$^{-1}$) |
|---|---|---|
| Na monostyryl-p-cresol(8 EO) ether sulfonate | 4.0 | 1.2 |
| Na distyryl-p-cresol(17 EO) ether sulfonate | 4.1 | 1.7 |

Example 5
Interfacial tension according to Du Nouy (mNm$^{-1}$)
at 40° C., pH 6.5, AS = 0.5%

| | Dist. water/n-octane (29.8/40.4 mNm$^{-1}$) | 50 g/l of NaCl/n-octane (32.8 mNm$^{-1}$) |
|---|---|---|
| Na monostyryl-p-cresol(8 EO) ether sulfonate | 8.9 | 6.0 |
| Na distyryl-p-cresol(17 EO) ether sulfonate | 9.9 | 6.7 |

Example 6
Na mono-/di-styrylcresol ether sulfonate

| | NaCl/CaCl$_2$ (g/l) | Temperature | Solubility | Interfacial tension spinning drop | Microcapillary oil removal | Phase behavior (middle phase formation) |
|---|---|---|---|---|---|---|
| Na distyryl-o-cresol(6 EO) sulfonate | 140/60 | 25° C. | + | ca. 10$^{-2}$ mNm$^{-1}$ | 9 | + |
| | 150/0 | 40° C. | + | ca. 10$^{-2}$ mNm$^{-1}$ | 9 | + |
| Na distyryl-o-cresol(13 EO) sulfonate | 180/20 | 40° C. | + | ca. 10$^{-2}$ mNm$^{-1}$ | 9 | + |
| Na distyryl-o-cresol(8 EO) sulfonate | 140/60 | 60° C. | + | ca. 10$^{-2}$ mNm$^{-1}$ | 8 | + |
| Na distyryl-o-cresol(19 EO) sulfonate | 150/0 | 60° C. | + | ca. 10$^{-2}$ mNm$^{-1}$ | 9 | + |
| Paraffin oil Na distyryl-p-cresol(6 EO) sulfonate | 150/0 | 25° C. | + | ca. 10$^{-2}$ mNm$^{-1}$ | 8 | + |
| K oil Na distyrylphenol-(15 EO) suflonate | 150/0 | 25° C. | + | ca. 10$^{-2}$ mNm$^{-1}$ | 6 | + |

Example 7

| Na distyryl-o-cresol(8 EO) sulfonate | Na dodecyl-benzene-sulfonate | Interfacial tension (spinning drop) mNm$^{-1}$ reservoir oil K, 35/15 g/l of NaCl/CaCl$_2$ | | | |
|---|---|---|---|---|---|
| | | 25° C. | 40° C. | 60° C. | 80° C. |
| 0.5% | 0.5% | $1 \cdot 10^{-2}$ | $1 \cdot 10^{-2}$ | $3 \cdot 10^{-2}$ | $4 \cdot 10^{-2}$ |
| 0% | 1% | *— | — | — | — |

*Solutions not measurable or not effective

Example 8

| Na distyryl-o-cresol (8 EO) sulfonate | Na sec-alkane-sulfonate MW 328 | Interfacial tension (spinning drop) mNm$^{-1}$ reservoir oil K, 70/30 g/l of NaCl/CaCl$_2$ | | | |
|---|---|---|---|---|---|
| | | 25° C. | 40° C. | 60° C. | 80° C. |
| 0.5% | 0.5% | $5 \cdot 10^{-2}$ | $2 \cdot 10^{-2}$ | $2 \cdot 10^{-2}$ | $4 \cdot 10^{-2}$ |
| 0% | 1% | *— | — | — | — |

*Solutions not measurable or not effective

Example 9

| Na distyryl-o-cresol(8 EO) sulfonate | Na dodecyl-benzene-sulfonate | Interfacial tension (spinning drop) mNm$^{-1}$ reservoir oil K, 90/10 g/l of NaCl/CaCl$_2$ | | |
|---|---|---|---|---|
| | | 40° C. | 60° C. | 80° C. |
| 0.5% | 0.5% | $3 \cdot 10^{-2}$ | $2 \cdot 10^{-2}$ | $2 \cdot 10^{-2}$ | $5 \cdot 10^{-2}$ |
| 0% | 1% | *— | — | — |

*Solutions not measurable or not effective

Example 10

| Na distyryl-o-cresol (8 EO) sulfonate | Na dodecyl-benzene-sulfonate | Interfacial tension (spinning drop) mNm$^{-1}$ reservoir oil K, 100 g/l of NaCl, pH 6.5 | | | |
|---|---|---|---|---|---|
| | | 25° C. | 40° C. | 60° C. | 80° C. |
| 0.5% | 0.5% | $1 \cdot 10^{-2}$ | $4 \cdot 10^{-2}$ | $3 \cdot 10^{-2}$ | $3 \cdot 10^{-2}$ |
| 0% | 1% | *— | — | — | — |

*Solutions not measurable or not effective

Example 11

| Na distyryl-o-cresol(13 EO) sulfonate | Na dodecylbenzene-sulfonate | Interfacial tension (spinning drop) mNm$^{-1}$ reservoir oil K, 90/10 g/l of NaCl/CaCl$_2$ | | | |
|---|---|---|---|---|---|
| | | 25° C. | 40° C. | 60° C. | 80° C. |
| 0.5% | 0.5% | $4 \cdot 10^{-2}$ | $9 \cdot 10^{-3}$ | $2 \cdot 10^{-2}$ | $7 \cdot 10^{-2}$ |
| 0% | 1% | *— | — | — | — |

*Solutions not measurable or not effective

Example 12

| Na distyryl-p-cresol (6 EO) sulfonate | Na dodecylbenzene-sulfonate | Interfacial tension (spinning drop) mNm$^{-1}$ reservoir oil I, 200 g/l of NaCl | | | |
|---|---|---|---|---|---|
| | | 25° C. | 40° C. | 60° C. | 80° C. |
| 0.5% | 0.5% | $1 \cdot 10^{-2}$ (+) | $6 \cdot 10^{-2}$ (+) | $7 \cdot 10^{-2}$ (+) | $2 \cdot 10^{-2}$ (+) |
| 0% | 1% | *— | — | — | — |

(+) denotes formation of a middle phase
*Solutions not measurable or not effective

Example 13

| Na distyryl-o-cresol (6 EO) sulfonate | Na dodecylbenzene-sulfonate | Interfacial tension (spinning drop) mNm$^{-1}$ reservoir oil K, 140/60 g/l of NaCl/CaCl$_2$ | | | |
|---|---|---|---|---|---|
| | | 25° C. | 40° C. | 60° C. | 80° C. |
| 0.5% | 0.5% | ca. $10^{-2}$ | ca. $10^{-2}$ | ca. $10^{-2}$ | ca. $10^{-2}$ |
| 0% | 1% | *— | —· | — | — |

*Solutions not measurable or not effective

Example 14

| Na distyryl-o-cresol (13 EO) sulfonate | Na dodecylbenzene-sulfonate | Interfacial tension (spinning drop) mNm$^{-1}$ reservoir oil K, 70/30 g/l of NaCl/CaCl$_2$ | | | |
|---|---|---|---|---|---|
| | | 25° C. | 40° C. | 60° C. | 80° C. |
| 0.5% | 0.5% | $1 \cdot 10^{-2}$ | $1 \cdot 10^{-2}$ | $3 \cdot 10^{-2}$ | $8 \cdot 10^{-2}$ |
| 0% | 1% | *— | — | — | — |

*Solutions not measurable or not effective

Example 15

| Na distyryl-o-cresol (6 EO) sulfonate | Na sec-alkane-sulfonate | Interfacial tension (spinning drop) mNm$^{-1}$ reservoir oil K, 200 g/l of NaCl/l | | | |
|---|---|---|---|---|---|
| | | 25° C. | 40° C. | 60° C. | 80° C. |
| 0.5% | 0.5% | $1 \cdot 10^{-2}$ | $3 \cdot 10^{-2}$ | $1 \cdot 10^{-2}$ | $2 \cdot 10^{-2}$ |
| 0% | 1% | *— | — | — | — |

*Solutions not measurable or not effective

Example 16

| Na distyryl-o-cresol (6 EO) sulfonate | Na dodecylbenzene-sulfonate | Interfacial tension (spinning drop) mNm$^{-1}$ reservoir oil II, 150 g of NaCl/l | | | |
|---|---|---|---|---|---|
| | | 25° C. | 40° C. | 60° C. | 80° C. |
| 0.5% | 0.5% | $2 \cdot 10^{-2}$ (6/+) | $3 \cdot 10^{-}$ (6/+) | $2 \cdot 10^{-2}$ (6/+) | $3 \cdot 10^{-3}$ (9/+) |
| 0% | 1% | *— | — | — | — |

The numbers 6 and 9 indicate the values measured in microcapillary oil removal; (+) denotes formation of a middle phase
*Solutions not measurable or not effective

Example 17

| Na distyryl-p-cresol (18 EO) sulfonate | Na sec-alkane-sulfonate | Interfacial tension (spinning drop) mNm$^{-1}$ reservoir oil I, 60° C. | |
|---|---|---|---|
| | | 180/20 g/l of NaCl/CaCl$_2$ | 140/60 g/l of NaCl/CaCl$_2$ |
| 0.5% | 0.5% | $6 \cdot 10^{-2}$ | $4 \cdot 10^{-2}$ |
| 0% | 1% | *— | — |

*Solutions not measurable or not effective

Example 18

| Na distyryl-o-cresol (6 EO) sulfonate | Na sec-alkane-sulfonate | Interfacial tension (spinning drop) mNm$^{-1}$ reservoir oil II, 135/15 g/l of NaCl/CaCl$_2$ | | | |
|---|---|---|---|---|---|
| | | 25° C. | 40° C. | 60° C. | 80° C. |
| 0.5% | 0.5% | $1 \cdot 10^{-2}$ (2/—) | $2 \cdot 10^{-1}$ (0/+) | $5 \cdot 10^{-2}$ (9/+) | $3 \cdot 10^{-3}$ |
| 0% | 1% | *— | — | — | — |

The numbers 0.2 or 9 indicate the values measured in microcapillary oil removal; (+) or (—) denotes that a middle phase has formed or has not formed.
*Solutions not measurable or not effective

Example 19

| Na distyryl-p-cresol(11 EO) sulfonate | Na sec-alkane-sulfonate | Interfacial tension (spinning drop) mNm$^{-1}$ reservoir oil I, 200 g/l of NaCl | | |
|---|---|---|---|---|
| | | 40° C. | 60° C. | 80° C. |
| 0.5% | 0.5% | $5 \cdot 10^{-2}$ (8/+) | $1 \cdot 10^{-2}$ (9/+) | $6 \cdot 10^{-2}$ (8/+) |
| 0% | 1% | *— | — | — |

The numbers 8 and 9 indicate the values measured in microcapillary oil removal; (+) denotes formation of a middle phase.
Solutions not measurable or not effective

Example 20

| Na distyryl-o-cresol(6 EO) sulfonate | Na sec-alkane-sulfonate | Interfacial tension (spinning drop) mNm$^{-1}$ reservoir oil I,105/45 g/l of NaCl/CaCl$_2$ | | | |
|---|---|---|---|---|---|
| | | 25° C. | 40° C. | 60° C. | 80° C. |
| 0.5% | 0.5% | $10^{-1}$ (0/—) | $10^{-1}$ (0/—) | $10^{-2}$ (8/+) | $10^{-2}$ (6/+) |
| 0% | 1.0% | *— | — | — | — |

The numbers 0.6 and 8 indicate the values measured in microcapillary oil removal; (+) or (—) denotes that a middle phase has formed or has not formed.
Solutions not measurable or not effective

Example 21

| Na monostyryl-p-cresol(8 EO) sulfonate | Na sec-alkane-sulfonate | Interfacial tension (spinning drop) mNm$^{-1}$ reservoir oil I, 105/45 g/l of NaCl/CaCl$_2$ | |
|---|---|---|---|
| | | 60° C. | 80° C. |
| 0.5% | 0.5% | $4 \cdot 10^{-2}$ | $6 \cdot 10^{-2}$ |
| 0% | 1% | *— | — |

*Solutions not measurable or not effective

Example 22

Interfacial tension (spinning drop) mNm$^{-1}$

| Na distyryl-p-cresol(8 EO) sulfonate | Na sec-alkane-sulfonate | reservoir oil 25° C. | I, 200 g of NaCl/l 40° C. | 60° C. | 80° C. |
|---|---|---|---|---|---|
| 0.5% | 0.5% | 10$^{-2}$ | 10$^{-2}$ | 1·10$^{-2}$ (8/+) | 3·10$^{-2}$ (9/+) |
| 0% | 1% | *— | — | — | — |

The numbers 8 and 9 indicate the values measured in microcapillary oil removal;
(+) denotes formation of a middle phase.
*Solutions not measurable or not effective

Example 23

Synergistic surfactant combinations 70/30 g/l of NaCl/CaCl$_2$, reservoir oil I, pH 6.5 (interfacial tension/microcapillary oil removal/solubility/phase behavior)

| Na distyryl-o-cresol (13 EO) sulfonate | Na dodecyl-benzene-sulfonate | Na petroleum-sulfonate (MW 420) | 25° C. | 40° C. | 60° C. | 80° C. |
|---|---|---|---|---|---|---|
| 0.7% | 0.25% | 0.05% | sol. (−) | sol. (−) | sol. (−) | sol. (−) |
| 0.55% | 0.40% | 0.05% | 5·10$^{-2}$ (6/+) | 4·10$^{-2}$ (8/+) | 6·10$^{-2}$ (9/+) | 4·10$^{-2}$ (9/+) |
| 0.50% | 0.25% | 0.25% | sol. (−) | sol. (−) | sol. (−) | sol. (−) |
| 0.40% | 0.45% | 0.15% | 3·10$^{-2}$ (6/+) | 4·10$^{-2}$ (9/+) | 4·10$^{-2}$ (9/+) | 6·10$^{-2}$ (9/+) |
| 0.30% | 0.05% | 0.05% | 7·10$^{-3}$ (6/+) | 4·10$^{-2}$ (9/+) | 4·10$^{-2}$ (9/+) | 5·10$^{-2}$ (9/+) |

The numbers 6, 8 and 9 indicate the values measured in microcapillary oil removal; (+) or (−) indicate that a middle phase has formed or has not formed.

Example 24

Synergistic surfactant combinations 200 g/l of NaCl, reservoir oil I, pH 6.5 (interfacial tension/microcapillary oil removal/solubility/phase behavior) 40° C.

| Na distyryl-p-cresol(11 EO) sulfonate | Na sec-alkane sulfonate | Na petroleum-sulfonate | 40° C. |
|---|---|---|---|
| 0.7% | 0.25% | 0.05% | 8·10$^{-2}$ (3) |
| 0.45% | 0.45% | 0.1% | 8·10$^{-3}$ (6) |
| 0.3% | 0.65% | 0.05% | 4·10$^{-2}$ (3) |

The numbers 3 and 6 indicate the values measured in microcapillary oil removal.

Example 25

Synergistic surfactant combinations 200 g/l of NaCl, reservoir oil I, pH 6.5 (interfacial tension/microcapillary oil removal/solubility/phase behavior

| Na distyryl-p-cresol(11 EO) sulfonate | Na sec-alkane-sulfonate | Na alkylxylene-sulfonate | °C. | 40° C. | 60° C. | 80° C. |
|---|---|---|---|---|---|---|
| 0.4% | 0.4% | 0.2% | 1·10$^{-2}$ (6) | 9·10$^{-3}$ (6) | 9·10$^{-3}$ (6) | 1·10$^{-2}$ (6) |
| | | | 7·10$^{-3}$ (8) | 8·10$^{-3}$ (8) | 1·10$^{-2}$ (6) | 1·10$^{-2}$ (6) |

The numbers 6 and 8 indicate the values measured in microcapillary oil removal.

Example 26

Synergistic surfactant combinations 70/30 g/l of NaCl/CaCl$_2$, reservoir oil I (interfacial tension/microcapillary oil removal/solubility/phase behavior) 40° C.

| Na distyryl-o-cresol(13 EO) sulfonate | Na C$_{14}$-C$_{16}$—olefin-sulfonate | |
|---|---|---|
| 0.5% | 0.5% | 2·10$^{-2}$ mNm$^{-1}$ (6/+) |

The number 6 indicates the value measured in microcapillary oil removal; (+) indicates formation of a middle phase The effectiveness of the compounds according to the invention was confirmed by laboratory flooding experiments with sand packs.

| Sand pack data: | |
|---|---|
| Sand: grain size | 0.03–0.15 mm |
| Length | 15 cm |
| Diameter | 3 cm |
| Pore volume | 41 cm$^3$ |
| Porosity | 48% |
| Permeability | 800 mDasy |
| Adhering water | 18% |
| Oil in place | 33.6 cm$^3$ |
| Surfactant slug | 20.5 cm$^3$; 2% of AS |
| Synthetic formation water: | |

| | |
|---|---|
| Experiment 1 + 2 | 70 g of NaCl/l + 30 g of CaCl$_2$/l |
| Experiment 3 + 4 | 200 g of NaCl/l |
| Temperature: | 80° C. |

Oil removal after water flooding using about four times the amount of the pore volume is about 70%. The oil remaining is set as residual oil saturation $S_r = 100\%$.

The increased oil removal is reproduced in the table below.

| | Surfactant systems | $S_R\%$ |
|---|---|---|
| (1) | 1.20% of Na distyryl-o-cresol(8 EO)-sulfonate/0.8% of Na sec-alkanesulfonate | 19.2 |
| (2) | 0.8% of Na distyryl-o-cresol(13 EO)-sulfonate/1.1% of Na sec-alkane sulfonate/0.1% of Na petroleumsulfonate/1% of sec-butanol | 45.3 |
| (3) | 1.20% of Na distyryl-p-cresol(11 EO)-sulfonate/0.8% of Na sec-alkanesulfonate | 21.0 |
| (4) | 1.07% of Na distyryl-p-cresol(11 EO)-sulfonate/0.74% of Na sec-alkanesulfonate/0.19% of Na petroleumsulfonate | 31.6 |

We claim:

1. A styrylaryloxy ether sulfonate of the formula

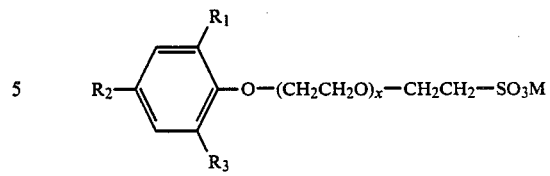

in which either $R_1$ denotes styryl and simultaneously $R_2$ and $R_3$ are identical or different and denote hydrogen or styryl, or $R_1$ and $R_2$ are nonidentical and each denote methyl or styryl and simultaneously $R_3$ denotes hydrogen or styryl, x denotes a number from 2 to 20, and M denotes an ammonium or alkali metal cation.

2. A styrylaryloxy ether sulfonate as claimed in claim 1, where $R_1$ and $R_2$ are nonidentical and each denote methyl or styryl, and $R_3$ denotes hydrogen or styryl, and x and M have the meanings mentioned in claim 1.

* * * * *